(12) United States Patent
Cavazza et al.

(10) Patent No.: US 9,114,120 B2
(45) Date of Patent: Aug. 25, 2015

(54) THERAPEUTICAL METHOD FOR THE TREATMENT OF THE LEBER OPTIC NEUROPATHY

(75) Inventors: Claudio Cavazza, Rome (IT); Anna Atti, legal representative, Rome (IT); Enrico Cavazza, legal representative, Rome (IT); Silvia Cavazza, legal representative, Rome (IT); Francesca Cavazza, legal representative, Rome (IT); Martina Cavazza, legal representative, Rome (IT); Aleardo Koverech, Rome (IT); Stefania D'Iddio, Ciampino (IT)

(73) Assignee: SIGMA-TAU INDUSTRIE FARMACEUTICHE RIUNITE, S.P.A., Rome (IT)

( * ) Notice: Subject to any disclaimer, the term of this patent is extended or adjusted under 35 U.S.C. 154(b) by 0 days.

(21) Appl. No.: 13/988,557

(22) PCT Filed: Sep. 9, 2011

(86) PCT No.: PCT/EP2011/065612
§ 371 (c)(1),
(2), (4) Date: Jul. 11, 2013

(87) PCT Pub. No.: WO2012/069221
PCT Pub. Date: May 31, 2012

(65) Prior Publication Data
US 2014/0051757 A1    Feb. 20, 2014

(30) Foreign Application Priority Data
Nov. 22, 2010 (EP) .................................. 10192001

(51) Int. Cl.
*A61K 31/221* (2006.01)
*A23L 1/305* (2006.01)
*A61K 31/205* (2006.01)
*A61K 45/06* (2006.01)

(52) U.S. Cl.
CPC ............. *A61K 31/221* (2013.01); *A23L 1/3051* (2013.01); *A61K 31/205* (2013.01); *A61K 45/06* (2013.01); *A23V 2002/00* (2013.01)

(58) Field of Classification Search
CPC ........................... A61K 31/221; A61K 31/205
See application file for complete search history.

(56) References Cited

U.S. PATENT DOCUMENTS 6,380,252 B1 * 4/2002 De Simone .................. 514/556
2010/0273894 A1 10/2010 Miller

OTHER PUBLICATIONS

CAS Registry No. 3040-38-8 (Nov. 16, 1984).*
Yen, May-Yung, An-Guor Wang, and Yau-Huei Wei. "Leber's hereditary optic neuropathy: a multifactorial disease." Progress in retinal and eye research 25.4 (2006): 381-396.*
Evans, Allan M., and Gianfranco Fornasini. "Pharmacokinetics of L-carnitine." Clinical pharmacokinetics 42.11 (2003): 941-967.*
Prayst, Igor, Katja Ž mitek, and Janko Ž mitek. "Coenzyme Q10 contents in foods and fortification strategies." Critical reviews in food science and nutrition 50.4 (2010): 269-280 (PMID: 20301015 (PubMed Abstract)).*
Newman, N. J., et al., Hereditary Optic Neuropathies, Eye, vol. 18, No. 11, pp. 1144-1160, 2004.
International Search Report in counterpart PCT/EP2011/065612.

* cited by examiner

*Primary Examiner* — Bethany Barham
*Assistant Examiner* — Peter Anthopolos
(74) *Attorney, Agent, or Firm* — Lucas & Mercanti, LLP

(57) ABSTRACT

It is described the use of L-carnitine and/or one or more alkanoyl L-carnitines, or mixture thereof, or one of their pharmaceutically acceptable salts, for the preparation of a medicament or a nutritional supplement useful for preventing or treating the Leber optic neuropathy.

11 Claims, No Drawings

THERAPEUTICAL METHOD FOR THE TREATMENT OF THE LEBER OPTIC NEUROPATHY

CROSS-REFERENCE TO RELATED APPLICATIONS

This application is a 371 of PCT/EP2011/065612, filed Sep. 9, 2011, which claims priority to and the benefit of European Patent Application No. EP10192001.5 filed Nov. 22, 2010, the contents of each of which are incorporated herein by reference.

The present invention relates to the use of L-carnitine and/or one or more alkanoyl L-carnitines, or mixture thereof, or one of their pharmaceutically acceptable salts, for the preparation of a medicament or a nutritional supplement useful for preventing or treating the Leber optic neuropathy (LHON) also known as Leber Optic Atrophy (LOA).

FIELD OF THE INVENTION

Leber hereditary optic neuropathy was first described in 1871 as a sudden loss of vision in young men with a family history of blindness. It is the most common of the hereditary Optic Atrophies.

LHON is an inherited form of vision loss due to degeneration of retinal ganglion cells (RGCs) and their axons. As discovered in 1988 LHON is one of a group of mitochondrial diseases, genetic diseases that are inherited only through the mother. [Science 1988; December 9; 242(4884):1427-30].

There are now some twenty different genes known to take part in the development of LHON. Three particular pathogenic mitochondrial DNA (mtDNA) point mutations account for 85% to 90% of the cases of LHON. These mutations are at nucleotide positions 11778 G to A, 3460 G to A and 14484 T to C, respectively in the ND4, ND1 and ND6 subunit genes of complex I of the oxidative phosphorylation chain in mitochondria.

However, the mitochondrial mutation is clearly not the only genetic factor involved in the disease, as not every carrier is affected.

In Northern European populations about one in 9000 people carry one of the three primary LHON mutations [Am. J. Hum. Genet. 2003; 72 (2): 333-9; Eur J Hum Genet 2007; 15 (10): 1079-89] and the prevalence of the disease in Europe is between 1:30,000 to 1:50,000. LHON typically presents in young adults as bilateral, painless, subacute visual failure. The median age of onset in LHON varies somewhat between series, but 95% of those who lose their vision do so by age 50 years. Rare cases may appear in early childhood and only very rarely, individuals first manifest LHON in the seventh decade of life [Eye 2007; 21: 859-60].

For unknown reasons males are approximately four times more frequently affected than females, but neither gender nor mutational status significantly influences the timing and severity of the initial visual loss.

Affected individuals are usually entirely asymptomatic until they develop blurring and clouding of vision. The visual blurring affecting the central vision (which is needed for detailed tasks such as reading, driving, and recognizing faces) may begin in one eye or simultaneously in both eyes; if vision loss starts in one eye, similar symptoms appear in the other eye an average of eight weeks later. In an estimated 25% of cases, visual loss is bilateral at onset. Over time, vision in both eyes worsens with a severe loss of sharpness (visual acuity) and colour vision.

Visual acuity is severely reduced to counting fingers or worse in most cases, and visual field testing (Goldmann perimetry or a similar technique) shows an enlarging central or centrocecal scotoma. After the acute phase, the optic discs become atrophic.

Although central vision gradually improves in a small percentage of cases, significant improvements in visual acuity are rare and, in most cases, the vision loss is profound and permanent.

Most persons affected by LHON qualify for registration as legally blind (visual acuity ≤20/200).

The diagnosis is based on ophthalmologic findings. Testing includes fundus examination, fluorescein angiography to identify characteristic vascular changes in the acute phase, Goldmann perimetry or a similar technique to identify the characteristic centrocecal scotoma, electrophysiologic studies (visual evoked potentials to confirm optic nerve dysfunction and pattern electroretinogram to confirm the absence of retinal disease), and cranial imaging to exclude other compressive, infiltrative, and inflammatory causes of a bilateral optic neuropathy.

Unfortunately, at present there is no cure for LHON and so far no treatment has been proven effective in controlled trials for LHON. However various agents and medications have been proposed, such us thiamin, coenzyme Q10, vitamin B2, vitamin K, vitamin C Vitamin A, Ginkgo biloba, and curcumin.

Previous uses of carnitine in the ophthalmological field are already known.

U.S. Pat. No. 5,037,851 describes the use of acetyl L-carnitine for the treatment of cataracts.

U.S. Pat. Nos. 5,145,871 and 5,432,199 describe the use of acetyl D-carnitine for the treatment of glaucoma.

U.S. Pat. No. 5,883,127 describes the use of acetyl L-carnitine for the treatment of maculopathy and macular degeneration.

Further uses of carnitine are also known.

In Res 1992; 18(8):355-365 the use of L-carnitine in the cardiological field is described.

U.S. Pat. No. 5,543,556 describes the use of acyl L-carnitine esters with gamma-hydroxybutyric acid for the inhibition of neuronal degeneration and in the treatment of coma.

U.S. Pat. No. 5,811,457 describes the use of propionyl L-carnitine for the treatment of chronic obliterating arteriopathy.

None of the above-cited patents or publications describes or suggests the use of L-carnitine or of alkanoyl L-carnitine for preventing or treating of Leber hereditary optic neuropathy.

In the medical field there is still a strongly perceived need for the availability of therapeutic agents or physiological supplement useful for the treatment of the Leber hereditary optic neuropathy disease.

DETAILED DESCRIPTION OF THE INVENTION

It has now been found that L-carnitine and/or one or more alkanoyl L-carnitines, or mixture thereof, or one of their pharmaceutically acceptable salts, are useful agents for the preparation of a medicament or a nutritional supplement useful for preventing or treating the Leber optic neuropathy.

It is therefore an object of the present invention the use of L-carnitine and/or one or more alkanoyl L-carnitines, or mixture thereof, or one of their pharmaceutically acceptable salts, for the preparation of a medicament or a nutritional supplement useful for preventing or treating the Leber hereditary optic neuropathy.

It is a further object of the present invention L-carnitine and/or one or more alkanoyl L-carnitines, or mixture thereof, or one of their pharmaceutically acceptable salts, for preventing or treating the Leber optic neuropathy.

It is a further object of the present invention a method for preventing or treating the Leber ptic neuropathy, which comprises administering to a patient in a need thereof a suitable amount of L-carnitine and/or one or more alkanoyl L-carnitines, or mixture thereof, or one of their pharmaceutically acceptable salts.

What is meant by pharmaceutically acceptable salt of L-carnitine or an alkanoyl L-carnitine is any salt of the latter with an acid that does not give rise to toxic or side effects.

These acids are well known to pharmacologists and to experts in pharmacy. Non-limiting examples of such salts are: chloride, bromide, orotate, aspartate, acid aspartate, acid citrate, magnesium citrate, phosphate, acid phosphate, fumarate and acid fumarate, magnesium fumarate, lactate, maleate and acid maleate, oxalate, acid oxalate, pamoate, acid pamoate, sulphate, acid sulphate, glucose phosphate, tartrate and acid tartrate, glycerophosphate, mucate, magnesium tartrate, 2-amino-ethanesulphonate, magnesium 2-amino-ethane-sulphonate, methanesulphonate, choline tartrate, trichloroacetate, and trifluoroacetate.

What is meant by pharmaceutically acceptable salt of L-carnitine is also a salt approved by the FDA and listed in the publication Int. J. of Pharm. 33 (1986), 201-217, which is incorporated herein by way of a reference.

The alkanoyl L-carnitine according to the present invention can be selected from the group consisting of acetyl, propionyl, valeryl, isovaleryl, butyryl and isobutyryl L-carnitine.

L carnitine or an alkanoyl L-carnitine, or mixture thereof, according to the present invention, can be administered enterally or parenterally in a dose of 0.2-4 g/day, a preferred dose is 0.5-3 g/day, the most preferred doses are 1 or 2 grams/day, in a single or divided dose. The oral administration is preferred.

The composition of the invention can be formulated as a pharmaceutical composition or as a nutritional supplement.

According to the present invention L-carnitine or an alkanoyl L-carnitine or mixture thereof, can be administered in combination with antioxidants, vitamins, mineral salts.

The following examples further illustrate the invention without limiting it.

Example 1

Visual Acuity Recovery and Visual Acuity Change

A group of 20 patients affected by LHON as assessed by the presence of at least one of the three most common pathogenic mutations (11778/ND4, 3460/ND1, 14484/ND6) were enrolled.

They were both sexes, with an age ≥18 years, and duration of disease greater than 2 years.

All the patients were treated orally with coenzyme Q10 (CoQ10) in combination with acetyl-L-carnitine or placebo for 12 months, according to a double blind study design. CoQ10 was administered at the dosage of 2 mg/day and ALC at the dosage of 1 g/day.

After 6 and 12 months of treatment all the patients were examined to evaluate the best recovery in visual acuity in either eye (measured by change in logMAR—logarithm of Minimal Angle of Resolution) and the best visual acuity.

The analysis performed comparing patients treated with coenzyme Q10 plus acetyl-L-carnitine with patients treated with coenzyme Q10 plus placebo showed a greater improvement of visual acuity recovery and visual acuity in the first group.

As reported in table 1, the difference between the two groups of patients was statistically significant only after 12 months of treatment (T12) but not after 6 months of treatment (T6) although there was a trend.

TABLE 1

| Population | Visual Acuity Recovery | | Visual Acuity Change | |
|---|---|---|---|---|
| | T6 | T12 | T6 | T12 |
| N = 20 (10-CoQ10 + ALC/10CoQ10 + placebo) | Diff = 8 letters $p < 0.07$ | Diff = 10 letters $p < 0.05$ | Diff = 10 letters $p < 0.07$ | Diff = 14 letters $p < 0.05$ |

Example 2

Visual Acuity Recovery and Visual Acuity Change

30 Patients with LHON were enrolled. To be eligible, participants were required to meet the following inclusion criteria: both sexes, age ≥20 years and ≤60 years, diagnosis of Leber's optic neuropathy assessed by the presence of at least one of the three most common LHON pathogenic mutations (11778/ND4, 3460/ND1, 14484/ND6), and duration of disease greater than 2 years.

The study treatment trial was 12-month, double blind, placebo controlled with participants randomized to receive acetyl L-carnitine (2 g/day orally) or placebo.

The primary efficacy end point for the study was the best recovery in visual acuity in either eye measured by change in logMAR (logarithm of Minimal Angle of Resolution) in study eyes comparing the acetyl-L-carnitine treatment group with the placebo treatment control group 6 and 12 months after enrolment. Secondary efficacy outcome was the patients' best visual acuity at 6 and 12 months compared to best visual acuity at baseline.

As reported in table 2, the analysis of the data performed at the end of the study showed a significant difference in improvement of visual acuity recovery between the patients receiving acetyl-L-carnitine and those receiving placebo either after 6 months of treatment (T6) either after 12 months of treatment (T12).

Also the visual acuity of eyes of patients receiving acetyl-L-carnitine significantly improved compared to those receiving placebo in both time points T6 and T12.

TABLE 2

| Population | Visual Acuity Recovery | | Visual Acuity Change | |
|---|---|---|---|---|
| | T6 | T12 | T6 | T12 |
| N = 30(15 + ALC/15 placebo) | Diff = 10 letters $p < 0.05$ | Diff = 12 letters $p < 0.01$ | Diff = 14 letters $p < 0.05$ | Diff = 18 letters $p < 0.01$ |

Note:
A difference of 5 letters is equivalent to 0.1 logMAR.

L-carnitine and its alkanoyl derivatives are known compounds, the preparation process for which is described in U.S. Pat. No. 4,254,053.

The pharmaceutical or nutritional composition according to the present invention may be bought with or without medical prescription and is composed of active ingredients which are familiar to operators in the medical field and already in use in clinical practice, and their pharmacotoxicological profiles are known.

Their procurement therefore is very easy, inasmuch as these are products which have been on the market now for a long time and are of a grade suitable for human or animal administration.

The invention claimed is:

1. Method for treating the Leber optic neuropathy, said method comprising orally administering to a patient suffering from Leber optic neuropathy an amount of L-carnitine and/or one or more alkanoyl L-carnitines, or mixture thereof, or one of their pharmaceutically acceptable salts, administered orally in a dose of 0.5-4 g/day, in a single or divided dose for 12 months, to treat the Leber optic neuropathy in said patient.

2. Method according to claim 1 in which the pharmaceutically acceptable salt of L-carnitine or an alkanoyl L-carnitine is selected from the group consisting of: chloride, bromide, orotate, aspartate, acid aspartate, acid citrate, magnesium citrate, phosphate, acid phosphate, fumarate and acid fumarate, magnesium fumarate, lactate, maleate and acid maleate, oxalate, acid oxalate, pamoate, acid pamoate, sulphate, acid sulphate, glucose phosphate, tartrate and acid tartrate, glycerophosphate, mucate, magnesium tartrate, 2-amino-ethanesulphonate, magnesium 2-amino-ethanesulphonate, methanesulphonate, choline tartrate, trichloroacetate, and trifluoroacetate.

3. Method according to claim 1 in which the alkanoyl L-carnitine is selected from the group consisting of: acetyl, propionyl, valeryl, iso valeryl, butyryl and isobutyryl L-carnitine.

4. Method according to claim 1 in which L-carnitine or the alkanoyl L-carnitine or mixture thereof, is administered in combination with antioxidants, vitamins and/or mineral salts.

5. Method according to claim 1 in which L-carnitine or the alkanoyl L-carnitine or mixture thereof, is administered as pharmaceutical composition or as a nutritional supplement.

6. Method of claim 1, wherein the dose is 0.5-3 g/day in a single or divided dose.

7. Method of claim 1, wherein the dose is 1 or 2 g/day in a single or divided dose.

8. Method according to claim 1, further comprising administering Coenzyme Q10 in combination with said L-carnitine and/or said one or more alkanoyl L-carnitines.

9. Method according to claim 8, wherein the L-carnitine or the alkanoyl L-carnitine or mixture thereof and Coenzyme Q10 are administered to the patient for 12 months.

10. Method of treating Leber optic neuropathy, consisting of orally administering a dose of 0.5-4 g/day, in a single or divided dose, of L-carnitine and/or one or more alkanoyl L-carnitines, or mixture thereof, or a pharmaceutically acceptable salt thereof and a dose of 2 mg per day of Coenzyme Q10 for 12 months to a patient suffering from Leber optic neuropathy and in a need thereof.

11. Method of claim 10, wherein the alkanoyl L-carnitine is acetyl L-carnitine administered at a dose of 1 gram/day and the Coenzyme Q10 is administered at a dose of 2 mg/day.

* * * * *